United States Patent
Mylari

(10) Patent No.: US 6,872,722 B2
(45) Date of Patent: Mar. 29, 2005

(54) THERAPIES FOR TISSUE DAMAGE RESULTING FROM ISCHEMIA

(75) Inventor: Banavara L. Mylari, Waterford, CT (US)

(73) Assignee: Pfizer Inc, New York, NY (US)

( * ) Notice: Subject to any disclaimer, the term of this patent is extended or adjusted under 35 U.S.C. 154(b) by 38 days.

(21) Appl. No.: 10/154,694

(22) Filed: May 23, 2002

(65) Prior Publication Data

US 2003/0008871 A1 Jan. 9, 2003

Related U.S. Application Data

(60) Provisional application No. 60/293,393, filed on May 24, 2001.

(51) Int. Cl.⁷ ..................... A61K 31/501; C07D 487/00
(52) U.S. Cl. .................... 514/252.01; 544/248
(58) Field of Search ....... 514/252.01–252.06, 514/248; 544/235–237, 248

(56) References Cited

U.S. PATENT DOCUMENTS

| | | | |
|---|---|---|---|
| 4,251,528 A | 2/1981 | Brittain et al. | 424/250 |
| 4,939,140 A | 7/1990 | Larson et al. | 514/222 |
| 4,996,204 A | 2/1991 | Mylari et al. | 514/248 |
| 5,506,228 A | 4/1996 | Norton et al. | 514/247 |
| 5,670,504 A | 9/1997 | Bochis et al. | 514/247 |
| 5,834,466 A | 11/1998 | Ramasamy et al. | 514/227.5 |
| 6,579,879 B2 * | 6/2003 | Mylari | 514/252.01 |
| 6,730,674 B2 * | 5/2004 | Martin et al. | 514/247 |
| 2003/0004139 A1 * | 1/2003 | Martin et al. | 514/85 |

FOREIGN PATENT DOCUMENTS

| | | | |
|---|---|---|---|
| EP | 1043317 | 10/2000 | C07D/237/04 |
| EP | 1236720 | 9/2002 | C07D/237/18 |

OTHER PUBLICATIONS

Tracey, et al., Am J. Physiol Heart Circ. Physiol, 279, pp. H1447–H1452, 2000.
Ramasamy, et al., Diabetes, vol. 46, Feb. 1997, pp. 292–300.
Patent Abstracts of Japan, vol. 014, No. 014 (C–674), 1990 & JP 01 258671A (Morishita Seiyaku KK), 1989, Abstract.

* cited by examiner

*Primary Examiner*—Dwayne Jones
(74) *Attorney, Agent, or Firm*—Peter C. Richardson; Gregg C. Benson; William F. Mulholland

(57) ABSTRACT

This invention relates to therapeutic methods for treatment or prevention of tissue damage resulting from ischemia in mammals.

24 Claims, No Drawings

THERAPIES FOR TISSUE DAMAGE RESULTING FROM ISCHEMIA

CROSS REFERENCE TO RELATED APPLICATION

This application claims the benefit of U.S. Provisional Application No. 60/293,393 filed May 24, 2001.

FIELD OF THE INVENTION

This invention relates to therapeutic methods for treatment or prevention of tissue damage resulting from ischemia in mammals.

BACKGROUND OF THE INVENTION

The enzyme aldose reductase is involved in regulating the reduction of aldoses, such as glucose and galactose, to their corresponding polyols, such as sorbitol and galactitol. Sulfonyl pyridazinone compounds of formula I of this invention are useful as aldose reductase inhibitors in the treatment and prevention of diabetic complications of humans and other mammals associated with increased polyol levels in certain tissues (e.g., nerve, kidney, lens and retina tissue) of affected humans and other mammals.

French Patent Publication No. 2647676 discloses certain pyridazinone derivatives having substituted benzyl side chains and benzothiazole side chains as being inhibitors of aldose reductase.

U.S. Pat. No. 4,251,528 discloses various aromatic carbocyclic oxophthalazinyl acetic acid compounds, as possessing aldose reductase inhibitory properties.

Commonly assigned U.S. Pat. No. 4,939,140 discloses heterocyclic oxophthalazinyl acetic acid compounds as aldose reductase inhibitors.

Commonly assigned U.S. Pat. No. 4,996,204 discloses pyridopyridazinone acetic acid compounds useful as aldose reductase inhibitors.

U.S. Pat. No. 5,834,466 discloses a method for limiting or decreasing the extent of ischemic damage due to metabolic and ionic abnormalities of the heart tissue resulting from ischemic insult by treatment with a compound such as an aldose reductase inhibitor which reduces the NADH/NAD+ ratio and stimulates glycolysis to produce ATP.

SUMMARY OF THE INVENTION

This invention provides therapeutic methods comprising administering to a mammal in need of treatment or prevention of tissue damage resulting from ischemia an effective amount of a compound of formula I

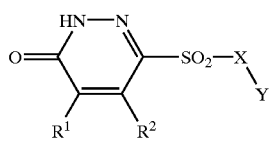

or a prodrug of said compound, or a pharmaceutically acceptable salt of said compound or said prodrug, wherein:

$R^1$ and $R^2$ are each independently hydrogen or methyl;

X and Y together are $CH_2$—$CH(OH)$—Ar or $CH_2$—$C(O)$—Ar, or

X is a covalent bond, $NR^3$ or $CHR^4$, wherein, $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^5R^6$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^5R^6$;

Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^5R^6$;

n is independently for each occurrence 0, 1 or 2;

$R^5$ is independently for each occurrence H, $(C_1-C_6)$alkyl, phenyl or naphthyl; and $R^6$ is independently for each occurrence $(C_1-C_6)$alkyl, phenyl or naphthyl.

In a preferred embodiment of this invention, said compound is selected from:

6-(3-trifluoromethyl-benzenesulfonyl)-2H-pyridazin-3-one;
6-(4-bromo-2-fluoro-benzenesulfonyl)-2H-pyridazin-3-one;
6-(4-trifluoromethyl-benzenesulfonyl)-2H-pyridazin-3-one;
6-(2-bromo-benzenesulfonyl)-2H-pyridazin-3-one;
6-(3,4-dichloro-benzenesulfonyl)-2H-pyridazin-3-one;
6-(4-methoxy-benzenesulfonyl)-2H-pyridazin-3-one;
6-(3-bromo-benzenesulfonyl)-2H-pyridazin-3-one;
6-(biphenyl-4-sulfonyl)-2H-pyridazin-3-one;
6-(4'-fluoro-biphenyl-4-sulfonyl)-2H-pyridazin-3-one;
6-(4'-trifluoromethyl-biphenyl-4-sulfonyl)-2H-pyridazin-3-one;
6-(3',5'-bis-trifluoromethyl-biphenyl-4-sulfonyl)-2H-pyridazin-3-one;
6-(biphenyl-2-sulfonyl)-2H-pyridazin-3-one;
6-(4'-trifluoromethyl-biphenyl-2-sulfonyl)-2H-pyridazin-3-one;
6-(2-hydroxy-benzenesulfonyl)-2H-pyridazin-3-one;
6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(4-fluoro-benzenesulfonyl)-2H-pyridazin-3-one;
6-(4-chloro-benzenesulfonyl)-2H-pyridazin-3-one;
6-(2-fluoro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one, or a prodrug of a compound selected therefrom, or a pharmaceutically acceptable salt of said compound or said prodrug.

In a more preferred embodiment of this invention, said compound is selected from:

6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(4-fluoro-benzenesulfonyl)-2H-pyridazin-3-one;
6-(4-chloro-benzenesulfonyl)-2H-pyridazin-3-one;
6-(2-fluoro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and 6-(naphthalene-1-sulfonyl)-2H-pyridazin-3-one, or a prodrug of a compound selected therefrom, or a pharmaceutically acceptable salt of said compound or said prodrug.

In an even more preferred embodiment of this invention, said compound is selected from:
6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one;
6-(2,5-dichloro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one,
or a prodrug of a compound selected therefrom, or a pharmaceutically acceptable salt of said compound or said prodrug.

In an especially more preferred embodiment of this invention, said compound is selected from:
6-(2,3-difluoro-benzenesulfonyl)-2H-pyridazin-3-one;
6-(2,4-dichloro-benzenesulfonyl)-2H-pyridazin-3-one;
6-(2-bromo-4-fluoro-benzenesulfonyl)-2H-pyridazin-3-one; and
6-(naphthalene-1-sulfonyl)-2H-pyridazin-3-one, or a prodrug of a compound selected therefrom, or a pharmaceutically acceptable salt of said compound or said prodrug.

In another preferred embodiment of this invention, said tissue is heart, brain, liver, kidney, lung, gut, skeletal muscle, spleen, pancreas, retina or intestinal tissue, preferably heart tissue.

In an additional preferred embodiment of this invention, said compound of formula I, said prodrug, or said pharmaceutically acceptable salt of said compound or said prodrug is administered in an aldose reductase inhibiting amount.

In a further preferred embodiment of this invention, said mammal is a human.

The term "compounds of this invention", as used herein means compounds of formula I. The term "compound(s) of formula I" is meant to include prodrugs of such compounds and pharmaceutically acceptable salts of such compounds and such prodrugs.

The term "$(C_1-C_t)$alkyl" as used herein, wherein the subscript "t" denotes an integer greater than 1, denotes a saturated monovalent straight or branched aliphatic hydrocarbon radical having one to t carbon atoms.

The terms "DMF", "DMSO" and "THF" mean N,N-dimethylformamide, dimethyl sulfoxide and tetrahydrofuran, respectively.

The expression "pharmaceutically acceptable salt" as used herein in relation to compounds of this invention includes pharmaceutically acceptable cationic salts. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, ethanolamine, diethanolamine, triethanolamine, ethylenediamine, meglumine (N-methylglucamine), benethamine (N-benzylphenethylamine), ethanolamine, diethylamine, piperazine, triethanolamine (2-amino-2-hydroxymethyl-1,3-propanediol) and procaine.

Pharmaceutically acceptable salts of the compounds of formula I of this invention may be readily prepared by reacting the free acid form of said compounds with an appropriate base, usually one equivalent, in a co-solvent. Preferred co-solvents include diethylether, diglyme and acetone. Preferred bases include sodium hydroxide, sodium methoxide, sodium ethoxide, sodium hydride, potassium methoxide, magnesium hydroxide, calcium hydroxide, benzathine, choline, ethanolamine, diethanolamine, piperazine and triethanolamine. The salt is isolated by concentration to dryness or by addition of a non-solvent. In many cases, salts may be prepared by mixing a solution of the acid with a solution of a different salt of the cation (e.g., sodium or potassium ethylhexanoate, magnesium oleate) and employing a co-solvent, as described above, from which the desired cationic salt precipitates, or can be otherwise isolated by concentration.

The term "prodrug" denotes a compound that is converted in vivo into a compound having a particular pharmaceutically activity. Such compounds include N-alkyl derivatives of formula I compounds as well as O-alkyl derivatives of formula I tautomeric compounds.

The term "therapeutic method" is meant to include methods that are palliative as well as those that are preventive.

Those skilled in the art will recognize that the compounds of this invention can exist in several tautomeric forms. All such tautomeric forms are considered as part of this invention. For example, all of the tautomeric forms of the carbonyl moiety of the compounds of formula I are included in this invention. All enol-keto forms of compounds of formula I are included in this invention.

Those skilled in the art will also recognize that the compounds of this invention can exist in several diastereoisomeric and enantiomeric forms. All diastereoisomeric and enantiomeric forms, and racemic mixtures thereof, are included in this invention.

Those skilled in the art will further recognize that the compounds of formula I can exist in crystalline form as hydrates wherein molecules of water are incorporated within the crystal structure thereof and as solvates wherein molecules of a solvent are incorporated therein. All such hydrate and solvate forms are considered part of this invention.

This invention also includes isotopically-labeled compounds, which are identical to those described by formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the schemes and/or in the Examples below, by substituting a readily available isotopically labeled reagent for a non-isotopically labeled reagent.

DETAILED DESCRIPTION OF THE INVENTION

The compounds of formula I of the present invention inhibit aldose reductase, an enzyme that catalyzes the bioconversion of glucose to sorbitol.

Scheme A

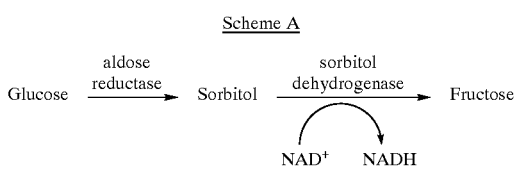

As shown in Scheme A, glucose is reduced to sorbitol by aldose reductase and sorbitol is then oxidized to fructose by sorbitol dehydrogenase. The conversion of sorbitol to fructose consumes $NAD^+$ (nicotinamide adenine dinucleotide). The compounds of formula I of this invention spare $NAD^+$ by reducing the level of sorbitol available for conversion to fructose.

When the supply of oxygenated blood to a tissue is reduced or interrupted (ischemia), the cells in the oxygen-deficient tissue are able to derive their energy anaerobically from glucose via the glycolysis pathway. Glycolysis requires the availability of $NAD^+$.

While not wishing to be bound by any particular theory or mechanism, it is believed that sparing $NAD^+$ use by aldose reductase inhibitors will enhance or prolong the ability of ischemic tissue to carry out glycolysis, i.e., to produce energy in the absence of oxygen and in turn enhance and prolong the survival of the cells in the tissue. Since, inhibition of aldose reductase will retard depletion of the tissue's $NAD^+$, an aldose reductase inhibitor is an effective anti-ischemic agent.

In general, the compounds of formula I of this invention may be prepared by methods that include processes analogous to those known in the chemical arts, particularly in light of the description contained herein. Certain processes for the manufacture of the compounds of formula I of this invention are illustrated by the following reaction schemes. Other processes are described in the experimental section.

Scheme 1

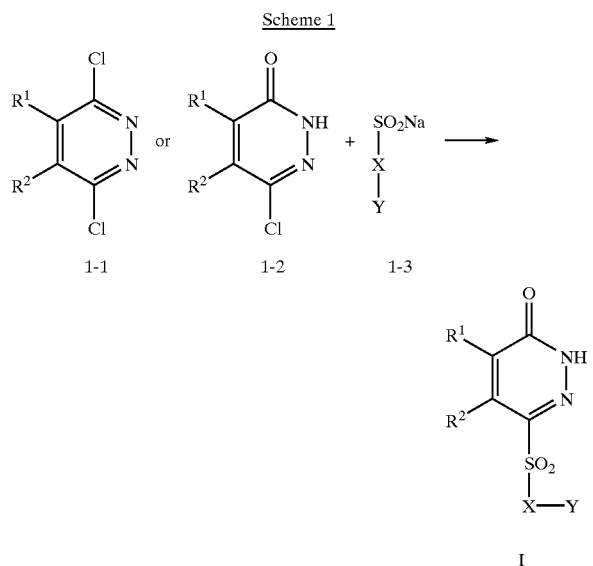

According to Scheme 1, compounds of formula I may be prepared by reacting dichloro pyridazine compounds of formula 1—1 or chloropyridazinone compounds of formula 1-2 with an alkali or alkali metal salt of Y—X—$SO_2$H, for example, Y—X—$SO_2$Na of formula 1-3, wherein $R^1$, $R^2$, X and Y are as defined herein. The reaction may be carried out in water or a mixture of water and water-miscible solvents such as dioxane or tetrahydrofuran (THF). The reaction is usually conducted at ambient pressure and at temperatures between about 80° C. and the boiling point of the solvent used.

Scheme 2

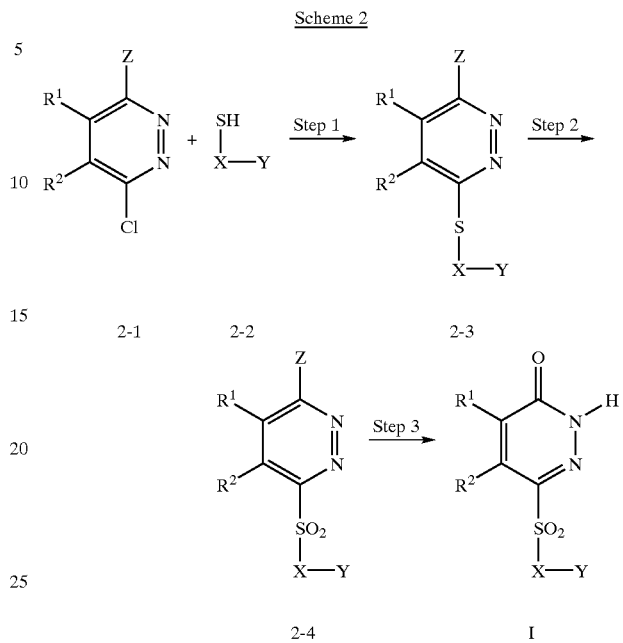

Compounds of formula I may also be prepared in accordance with the steps of Scheme 2. In step 1 of Scheme 2, a compound of formula 2-1, wherein $R^1$, $R^2$, X and Y are as defined herein and Z is Cl, O—$(C_1-C_6)$alkyl, O—Ph, O—$CH_2$—Ph, wherein Ph is phenyl optionally mono- or di-substituted with chlorine, bromine, or methyl, is reacted with a thiol compound of formula 2-2 to form the formula 2-3 sulfanyl compound.

In one method of step 1 of Scheme 2, a formula 2-1 compound is reacted with the alkali metal salt of a formula 2-2 thiol. The alkali metal salt is prepared by reacting the formula 2-2 thiol with an alkali metal $(C_1-C_6)$alkoxide in $(C_1-C_6)$alkyl-OH. It is preferable that the $(C_1-C_6)$alkoxide and the $(C_1-C_6)$alkyl-OH correspond to Z of the formula 2-1 compound. For example, when Z is OMe the preferred alkoxide is an alkali metal methoxide, preferably sodium methoxide, and the preferred $(C_1-C_6)$alkyl-OH is methanol. Potassium t-butoxide may be used in any combination of alkanol and Z. Preferred metal oxides are sodium methoxide and sodium ethoxide. Excess alcohol from the reaction forming the alkali metal salt of the formula 2-2 thiol compound is evaporated away and the resulting alkali metal salt is refluxed overnight in an aromatic hydrocarbon solvent, preferably toluene, together with the formula 2-1 compound to form the formula 2-3 compound.

In another method of step 1 of Scheme 2, compounds of formula 2-3 may be prepared by reacting compounds of formula 2-1 with compounds of formula 2-2 in N,N-dimethylformamide (DMF) containing sodium or potassium carbonate. The reaction is preferably conducted at ambient pressure and at a temperature of between about 60° C. and about 120° C.

In a further method of step 1 of Scheme 2, compounds of formula 2-1, wherein Z is O—$(C_1-C_6)$alkyl, are reacted with compounds of formula 2-2 either in a polar non-aqueous solvent (e.g., acetonitrile) or in an ether solvent (e.g., diglyme or tetrahydrofuran) or DMF containing alkali or alkali earth metal hydrides, preferably sodium hydride, or potassium t-butoxide. A preferred solvent is DMF.

Compounds of formula 2-1 of Scheme 2, wherein Z is O—$(C_1-C_6)$alkyl, O—Ph, O—$CH_2$—Ph, wherein Ph is phenyl optionally mono- or di-substituted with chlorine, bromine, or methyl, may be prepared by reacting a compound of formula 1—1

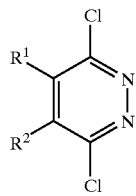

1-1 with the sodium salts of HO—($C_1$–$C_6$)alkyl, HO—Ph or HO—$CH_2$—Ph. The sodium salts may be prepared by reacting HO—($C_1$–$C_6$)alkyl, HO—Ph or HO—$CH_2$—Ph, as applicable, with sodium metal at a temperature of about 0° C. to about 50° C. The oxide may also be prepared by reacting HO—($C_1$–$C_6$)alkyl, HO—Ph or HO—$CH_2$—Ph with sodium hydride, optionally in the presence of a reaction-inert solvent, preferably benzene, toluene, THF or ether, at a temperature of between about 0° C. and about room temperature.

In step 2 of Scheme 2, a compound of formula 2-3 is oxidized to form the formula 2-4 sulfonyl compound. The formula 2-3 compounds may be oxidized with 30% hydrogen peroxide, optionally in the presence of formic acid, acetic acid or a peracid, such as m-chloroperbenzoic acid (MCPBA), in a halocarbon solvent (e.g., dichloromethane). The reaction is preferably conducted at ambient pressure and at a temperature of between about 20° C. and about 40° C., and is complete in about three to about six hours. The reaction should be monitored carefully to avoid over-oxidation of the nitrogen atoms to N-oxides. N-oxides that are formed may be converted to the reduced pyridazine compound by reacting the N-oxide with triethylphosphite, sodium sulfite or potassium sulfite, preferably at about 100° C. for about four hours.

The formula 2-4 compounds of step 3 of Scheme 2 are hydrolyzed with a mineral acid, e.g., concentrated hydrochloric acid, alone or in an ether solvents such as dioxane, to obtain a compound of formula I. The reaction of step 3 is preferably conducted at ambient pressure and at the refluxing temperature of the solvent used.

Scheme 3

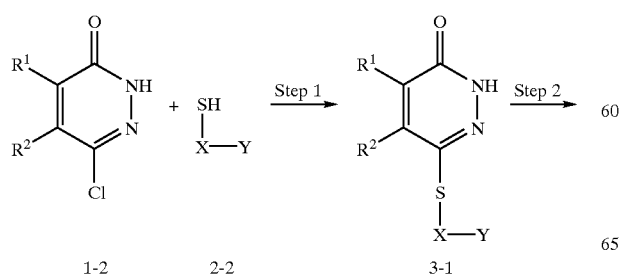

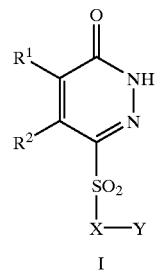

I

Scheme 3 provides still another method of preparing compounds of formula I. In Scheme 3, a chloropyridazinone compound of formula 1-2 is reacted with a thiol compound of formula 2-2 to form a sulfanylpyridazinone compound of formula 3-1. The reaction is preferably performed in the presence of an alkali or an alkali metal alkoxide, for example potassium tertbutoxide, in reaction-inert polar solvent such as DMF or acetonitrile at about room temperature to about 100° C. The resulting compound of formula 3-1 is oxidized with hydrogen peroxide, optionally in the presence of acetic acid or a peracid, preferably m-chloroperbenzoic acid (MCPBA), in a halocarbon solvent such as dichloromethane, to form a compound of formula I.

Scheme 4

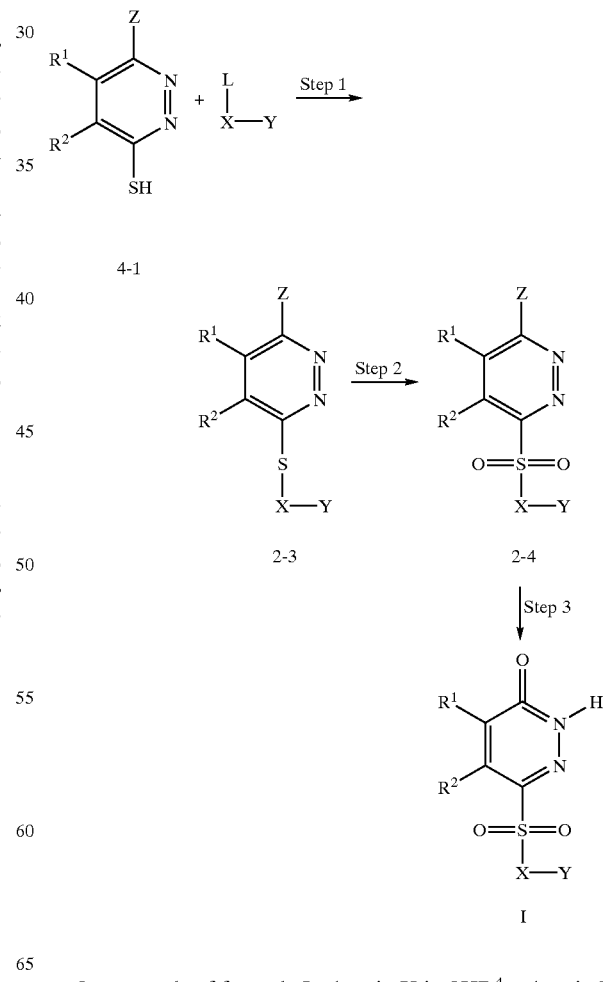

Compounds of formula I wherein X is $CHR^4$, wherein $R^4$ is hydrogen or methyl may be prepared according to Scheme 4. In step 1 of Scheme 4, a compound of formula 4-1, wherein Z is Cl, O—($C_1$–$C_6$)alkyl, O—$Ph^1$, O—$CH_2$—$Ph^1$, wherein $Ph^1$ is phenyl optionally mono- or di-substituted with chlorine, bromine, or methyl, is reacted with Y—X—L, wherein L is a leaving group, preferably Cl, Br, I, $OSO_2CH_3$, $OSO_2CF_3$, or $OSO_2Ph^2$, wherein $Ph^2$ is a phenyl optionally monosubtituted with Br, Cl or $OCH_3$, in the presence of a base, preferably sodium carbonate, potassium carbonate or sodium hydride to form a compound of formula 2-3. When the base is sodium carbonate or potassium carbonate, the reaction solvent is preferably acetone. However, if the base is sodium hydride, DMF or acetonitrile is used as the reaction solvent. The reaction is preferably conducted at ambient pressure and at a temperature of between about room temperature and about 100° C. Steps 2 and 3 are analogous to steps 2 and 3 of Scheme 2 and are conducted in the same manner thereof.

Compounds of formula I wherein X and Y together form —$CH_2C(O)Ar$ may be prepared according to Scheme 4 by reacting, in step 1, compounds of formula 4-1 with $LCH_2C(O)Ar$ to form a compound of formula 2-3. The reaction is conducted in the presence of a base, preferably sodium carbonate or potassium carbonate and in a reaction-inert solvent such as dimethyl formamide. The reaction temperature is preferably from about room temperature to about 80° C. Steps 2 and step 3 of Scheme 4 are performed in a manner analogous to steps 2 and 3 of Scheme 2.

Compounds of formula I wherein X and Y together form —$CH_2CH(OH)Ar$ may be prepared by reacting compounds of formula I wherein X and Y together form —$CH_2C(O)Ar$ with sodium borohydride in alcoholic solvents such as methanol, ethanol or isopropanol. The reaction is preferably conducted at a temperature of about 0° C. to about 60° C. and at ambient pressure.

Scheme 5

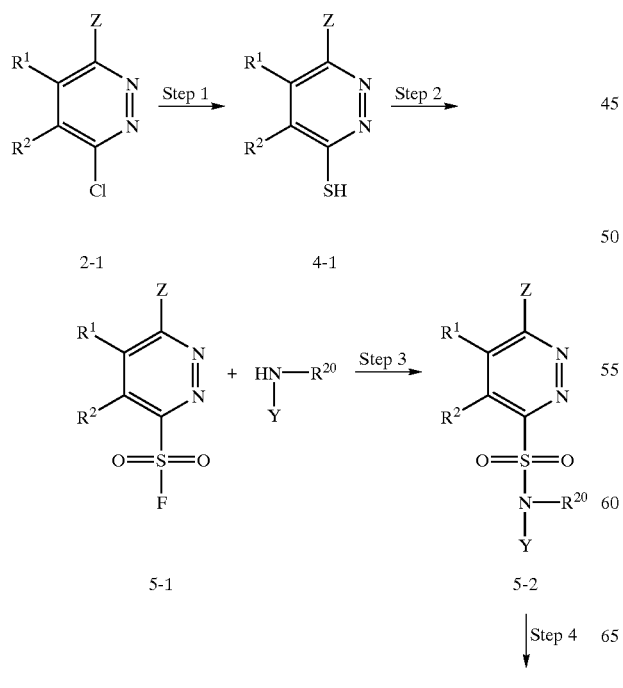

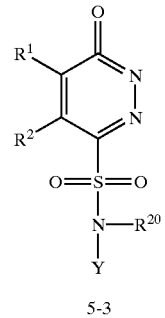

5-3

Compounds of formula I wherein X is $NR^{20}$ wherein $R^{20}$ is ($C_1$–$C_3$)alkyl (formula 5-3 compounds) may be prepared in accordance with Scheme 5. In step 1 of Scheme 5, a compound of formula 2-1, wherein Z is Cl, O—($C_1$–$C_6$) alkyl, O—Ph, O—$CH_2$—Ph, wherein Ph is phenyl optionally mono- or di-substituted with chlorine, bromine, or methyl, is reacted with thiourea in a ketone solvents, preferably acetone, ethyl methyl ketone or isobutyl ketone, to obtain a compound of formula 4-1. Step 1 is conducted at ambient pressure and at the refluxing temperature of the solvent. Compounds of formula 2-1 may be prepared as described above for Scheme 2.

In step 2 of Scheme 5, a compound of formula 5-1 is prepared according to the process disclosed in J. Heterocyclic Chem., 1998, 35, 429-436. Compounds of formula 5-1 are particularly useful as intermediates in the preparation of compounds of formula 1.

In Step 3 of Scheme 5, a formula 5-2 compound is prepared by reacting a compound of formula 5-1 with excess $HN(R^{20})$—Y, optionally in an organic reaction inert base, preferably a trialkyl amine selected from trimethylamine, triethylamine, and dimethyl-isopropyl-amines, more preferably triethylamine. The reaction may optionally be performed in a reaction inert solvent such as an ether, halocarbon or aromatic hydrocarbon solvent, preferably selected from diethyl ether, isopropyl ether, tetrahydrofuran, diglyme, chloroform, methylene dichloride, benzene and toluene. The reaction of step 3 is preferably performed at a temperature of about room temperature to about the refluxing temperature of the solvent that is used.

In step 4 of Scheme 5, a compound of formula 5-3 may be prepared by hydrolyzing a compound of formula 5-2 with a mineral acid such as concentrated hydrochloric acid, either alone or an ether solvent (e.g., dioxane). The reaction may be conducted at about room pressure to about the refluxing temperature of the solvent used.

Compounds of formula I wherein X is a covalent bond and Y is a phenyl or napthyl ring substituted with hydroxy may be prepared by reacting compounds of formula I wherein Y is phenyl or naphthyl substituted with $C_1$–$C_6$ alkoxy with a dealkylating reagents such as $AlCl_3$, $AlBr3$, or $BF_3$. When $AlCl_3$ or $AlBr_3$ are the dealkylating reagent, the reaction is preferably carried out without any solvent. When the dealkylating reagent is $BF_3$, a halocarbon solvent is preferably used, preferably methylene chloride or ethylene chloride. The reaction is conducted at ambient pressure and at temperatures between about −60° C. to about 80° C.

Compounds of formula I wherein X is a covalent bond and Y is phenyl or naphthyl substituted with an optionally substituted phenyl or naphthyl ring may be prepared by first reacting compounds of formula 2-4 wherein X is a covalent bond, Z is O—($C_1$–$C_6$)alkyl, Y is a phenyl or napthyl that has a bromo or iodo substitutent with an appropriately substituted phenyl or naphthyl boronic acid in the presence of a palladium catalyst such as $Pd[P(Ph)_3]_4$ and in the presence of either potassium carbonate or sodium carbonate.

The reaction is preferably conducted in an aromatic hydrocarbon solvent, preferably toluene, or in a $C_1$–$C_6$ alcohol, preferably ethanol, at ambient pressure and at a temperature of about room temperature to the refluxing temperature of the solvent used. The product of the first step is hydrolyzed with a mineral acid, preferably hydrochloric acid, alone or an ether solvent, preferably dioxane, to obtain a compound of formula I wherein Y is phenyl or naphthyl substituted with an optionally substituted phenyl or naphthyl ring.

Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described below demonstrates that a test compound (i.e., a compound as described herein) can also pharmacologically induce cardioprotection, i.e., reduce myocardial infarct size, when administered to a rabbit isolated heart. The effects of the test compound are compared to ischemic preconditioning and the A1/A3 adenosine agonist, APNEA 2-(4-aminophenyl) ethyl adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., id. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a branch of the left anterior descending coronary artery, approximately ⅔ of the distance towards the apex of the heart. The heart is removed from the chest and rapidly (<30 seconds) mounted on a Langendorff apparatus. The heart is retrogradely perfused via the aorta in a non-recirculating manner with a modified Krebs solution (NaCl 118.5 mM, KCl 4.7 mM, $MgSO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure ≦10 mmHg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at about 200 bpm for the remainder of the experiment. Ischemic preconditioning is induced by total cessation of cardiac perfusion (global ischemia) for 5 min, followed by reperfusion for 10 min. The global ischemia/reperfusion is repeated one additional time, followed by a 30 min regional ischemia. The regional ischemia is provided by tightening the snare around the coronary artery branch. Following the 30 min regional ischemia, the snare is released and the heart reperfused for an additional 120 min.

Pharmacological cardioprotection is induced by infusing the test compounds at predetermined concentrations, starting 30 min prior to the 30 ml regional ischemia, and continuing until the end of the 120 min reperfusion period. Hearts, which receive test compounds, do not undergo the two periods of ischemic preconditioning. The reference compound, APNEA (500 nM) is perfused through hearts (which do not receive the test compound) for a 5 min period which ends 10 minutes before the 30 minute regional ischemia.

At the end of the 120 minute reperfusion period, the coronary artery snare is tightened, and a 0.5% suspension of fluorescent zinc cadmium sulfate particles (1–10 μm) is perfused through the heart; this stains all of the myocardium, except that area at risk for infarct development (area-at-risk). The heart is removed from the Langendorff apparatus, blotted dry, weighed, wrapped in aluminum foil and stored overnight at −20° C. The next day, the heart is sliced into 2 mm transverse sections from the apex to just above the coronary artery snare. The slices are stained with 1% triphenyl tetrazolium chloride (TTC) in phosphate-buffered saline for 20 min at 37° C. Since TTG reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for difference in the area-at-risk between hearts, the data is expressed as the ratio of infarct area vs. area-at-risk (% IA/AAR).

The activity and thus utility of the compounds of the present invention as medical agents in providing protection from ischemic damage to tissue in a mammal can be further demonstrated by determining the aldose reductase inhibition activity of the compounds according to standard in vitro assays known to those skilled in the art (e.g., B. L. Mylari, et al., J. Med. Chem., 1991, 34, 108–122) and according to the protocol described in the General Experimental Procedures, hereinbelow. The activity of an aldose reductase inhibitor in a tissue can be determined by testing the amount of aldose reductase inhibitor that is required to lower tissue sorbitol levels or tissue fructose levels (i.e., by inhibiting the production of fructose from sorbitol as a result of inhibiting aldose reductase).

In the therapeutic method aspects of this invention, the compounds of formula I are administered as part of an appropriate dosage regimen designed to obtain the benefits of the therapy. The amount of each dose administered and the intervals between doses of the compound will depend upon the compound of formula I of this invention being used, the type of pharmaceutical compositions being used, the characteristics of the subject being treated and the severity of the conditions. Generally, in carrying out the methods of this invention, an effective dosage for the compounds of formula I of this invention is in the range of about 0.1 mg/kg/day to about 500 mg/kg/day in single or divided doses. However, some variation in dosage will necessarily occur depending on the condition of the subject being treated. The individual responsible for dosing will, in any event, determine the appropriate dose for the individual subject.

The in vitro assay and the in vivo protocol described herein provide a means whereby the activities of the compounds of this invention can be compared with the activities of other known compounds. The results of these comparisons are useful for determining dosage levels in mammals, including humans, for inducing protection from ischemia. Such assays provide a means to compare the activities of the compounds of formula I of this invention and other known compounds that are aldose reductase inhibitors. The results of these comparisons are useful for determining such dosage levels.

Administration of the compounds of this invention may be performed via any method which delivers a compound of this invention preferentially to the desired tissue (e.g., nerve, kidney, lens, retina and/or cardiac tissues). The compounds may be administered by a variety of routes of administration, including orally, intraduodenally, parenterally (e.g., intravenously, rectally, subcutaneously or by inhalation), etc., and may be administered in single (e.g., once daily) or multiple doses or via constant infusion.

The compounds of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

Buccal administration of a composition of this invention may take the form of tablets or lozenges formulated in a conventional manner.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

The journal articles and scientific references and patents publications cited above are wholly incorporated herein by reference.

GENERAL EXPERIMENTAL PROCEDURES

Melting points were determined on a Thomas-Hoover capillary melting point apparatus, and are uncorrected. $^1$H NMR spectra were obtained on a Bruker AM-250 (Bruker Co., Billerica, Mass.), a Bruker AM-300, a Varian XL-300 (Varian Co., Palo Alto, Calif.), or a Varian Unity 400 at about 23° C. at 250, 300, or 400 MHz for proton. Chemical shifts are reported in parts per million (δ) relative to residual chloroform (7.26 ppm), dimethylsulfoxide (2.49 ppm), or methanol (3.30 ppm) as an internal reference. The peak shapes and descriptors for the peak shapes are denoted as follows: s, singlet; d, doublet; t, triplet; q, quartet; m, multiplet; c, complex; br, broad; app, apparent. Low-resolution mass spectra were obtained under thermospray (TS) conditions on a Fisons (now Micromass) Trio 1000 Mass Spectrometer (Micromass Inc., Beverly, Mass.), under chemical-ionization (Cl) conditions on a Hewlett Packard 5989A Particle Beam Mass Spectrometer (Hewlett Packard Co., Palo Alto, Calif.), or under atmospheric pressure chemical ionization (APCI) on a Fisons Plafform II Spectrometer.

EXAMPLE 1

6-(3-Trifluoromethyl-benzenesulfonyl)-2H-pyridazin-3-one

A mixture of 3,6-dichloropyridazine (4.44 g), 3-trifluoromethylphenyl sulfinic acid sodium salt (6.93 g), isopropanol (30 mL), and water (1 mL) was prepared and refluxed for 18 hours. The reaction mixture was then cooled, diluted with water (100 mL) and the precipitated solid was collected. The solid was triturated with n-propanol and the solid was collected to obtain the title compound (25%, 2.3 g).

EXAMPLE 2

6-(2-Fluoro-benzenesulfonyl)-2H-pyridazin-3-one

Step A: 3-(2-Fluoro-phenylsulfanyl)-6-methoxy-pyridazine. To a clear solution of 4-fluorothiophenol (2.56 g) in DMF (10 mL) was added 3-chloro-6-methoxy-pyridazine (3.18 g) and stirred at room temperature for 1 hour. The reaction mixture was quenched with water (30 mL) and extracted with ethyl acetate (50 mL). The ethyl acetate layer was collected, washed with water (2×20 mL) and the organic portion was collected, dried over anhydrous sodium sulfate, filtered and the filtrate was evaporated to obtain crude 3-(2-fluoro-phenylsulfanyl)-6-methoxy-pyridazine (85%, 4.0g, mp, 58–62° C.; mass spectrum M$^+$, 236).

Step B: 3-(2-Fluoro-benzenesulfonyl)-6-methoxy-pyridazine. A mixture of 3-(2-fluoro-phenylsulfanyl)-6- methoxy-pyridazine (500 mg), m-chloroperbenzoic acid (MCPBA) (1.04 g) and methylene dichloride (10 mL) was prepared and stirred at room temperature for two hours. The reaction mixture was diluted with methylene dichloride and the methylene dichloride layer was washed with saturated sodium bicarbonate (10 mL) and then with water (2×20 mL). The methylene dichloride layer was collected, dried over anhydrous sodium sulfate, filtered and the filtrate was evaporated to dryness. The residue was purified by silica gel chromatography (3:1 ethyl acetate/hexane as eluent) to obtain 3-(2-fluoro-benzenesulfonyl)-6-methoxy-pyridazine as a white solid (51%, 290 mg; NMR, 4.19 (s, 3H), 7.13 (d, 1H), 7.21 (d, 1H), 8.13 (m, 4H).

Step C: 6-(2-Fluoro-benzenesulfonyl)-2H-pyridazin-3-one. A mixture of 3-(2-fluoro-benzenesulfonyl)-6-methoxy-pyridazine (200 mg) and concentrated hydrochloric acid (2 mL) was prepared and refluxed for one hour. The reaction mixture was cooled and diluted with water (20 mL). Sufficient 40% aqueous sodium hydroxide was then added to adjust the pH of the mixture to 3 and the mixture was extracted with ethyl acetate (2×20 mL). The ethyl acetate extract portions were collected and combined, dried over anhydrous sodium sulfate and filtered. The filtrate was evaporated to obtain the title compound as a white solid (45%, 80 mg), mp, 173–176° C.; NMR, 7.06 (d, 1H), 7.23 (m, 1H), 7.3 (m, 1H), 7.89 (d, 1H), 8.02 (m, 2H) and 11.66 (s, 1H).

EXAMPLE 3

6-(4-Bromo-2-fluoro-benzenesulfonyl)-2H-pyridazin-3-one

Step A: 3-(4-Bromo-2-fluoro-phenylsulfanyl)-6-methoxy-pyridazine. A mixture of 2-fluoro-4-bromothiophenol (300 mg), 2,6-dichloro-pyridazine (149 mg), potassium carbonate (400 mg) and acetone (6 mL) was prepared and refluxed for two hours. The acetone from the mixture was evaporated and the resulting residue was dissolved in a solution of methanol (3 mL) and sodium metal (166 mg). The resulting solution was refluxed for 1 hour. Evaporation of methanol afforded 3-(4-bromo-2-fluoro-phenylsulfanyl)-6-methoxy-pyridazine, which was not isolated but was immediately used in Step 2.

Step B: 3-(4-Bromo-2-fluoro-benzenesulfonyl)-6-methoxy-pyridazine. The product of Step A (400 mg) was dissolved in chloroform (10 mL) and m-chloroperbenzoic acid (MCPBA) (770 mg) was added to the resulting solution. The reaction mixture was stirred overnight at room temperature. The solvent was evaporated and the resulting residue was purified by silica gel chromatography (90% hexane/10% ethyl acetate as eluent) to obtain the title compound (264 mg, 60%): mass spectrum, M$^+$, 346.

Step C: 6-(4-Bromo-2-fluoro-benzenesulfonyl)-2H-pyridazin-3-one. A mixture of 3-(4-bromo-2-fluoro-benzenesulfonyl)-6-methoxy-pyridazine (260 mg), dioxane (5 mL), and concentrated hydrochloric acid (1 mL) was prepared and refluxed for two hours. The reaction mixture was then evaporated to dryness. The resulting residue was triturated with water and the precipitated solid was collected and air-dried to obtain the title compound (90%, 225 mg); mp, >220° C.; NMR 7.05 (d, 1H), 7.7 (d, 1H), 7.9 (m, 3H), 13.8 (s, 1H).

EXAMPLE 4

6-(3-Chloro-benzenesulfonyl)-2H-pyridazin-3-one
Step A: 3-(3-Chloro-phenylsulfanyl)-6-methoxy-pyridazine. Sodium metal (218 mg) was dissolved in methanol (10 mL). 3-Chlorothiophenol was added and stirred for one hour at room temperature. The excess methanol was evaporated and to the dry residue was added toluene (20 mL) and 3-chloro-6-methoxypyridazine (1.1 g). The reaction mixture was refluxed for four hours, cooled to room temperature and then poured into water (30 mL). The pH of the solution was first adjusted to 10 with 20% potassium hydroxide and extracted with ethyl acetate (2×20 mL). The aqueous layer from the extraction was collected. The aqueous portion was acidified to pH 3 with concentrated hydrochloric acid and then extracted with ethyl acetate (3×10 mL). The ethyl acetate extract was evaporated and the residue was purified by silica gel chromatography to afford 3-(3-chloro-phenylsulfanyl)-6-methoxy-pyridazine (M$^+$, 253).

Step B: 3-(3-Chloro-benzenesulfonyl)-6-methoxy-pyridazine. A mixture of 3-(3-chloro-phenylsulfanyl)-6-methoxy-pyridazine (529 mg), m-chloroperbenzoic acid (MCPBA) (760 mg) and chloroform (20 mL) was prepared and stirred at room temperature for two hours. The reaction mixture was diluted with 5% sodium thiosulfate (20 mL) followed by water (30 mL). The chloroform layer was collected, dried over anhydrous sodium sulfate, filtered and the dried chloroform portion was evaporated to dryness. The resulting solid residue was purified by silica gel chromatography (3:1 hexane/ethyl acetate as eluent) to obtain 3-(3-chloro-benzenesulfonyl)-6-methoxy-pyridazine (29%, 173 mg); mass spectrum, M$^+$, 285.

Step C: 6-(3-Chloro-benzenesulfonyl)-2H-pyridazin-3-one. A mixture of 3-(3-chloro-benzenesulfonyl)-6-methoxy-pyridazine (148 mg), dioxane (2 mL) and concentrated hydrochloric acid (0.5 mL) was prepared and refluxed for 30 minutes. The reaction mixture was then evaporated to dryness and the residue was extracted with ethyl acetate (2×10 mL). The ethyl acetate mixture was collected, dried over anhydrous sodium sulfate, filtered and the filtrate was evaporated to dryness to afford 6-(3-chloro-benzenesulfonyl)-2H-pyridazin-3-one as white solid (38%, 61 mg); mp, 222–223° C.: NMR, 7.11 (d, 1H), 7.74 (t, 1H), 7.86–8.04 (m, 4H), 13.86 (s, 1H).

Examples 4A to 4N were prepared from the appropriate starting materials in a manner analogous to the method of Example 4.

| Example | Compound | MP ° C. |
| --- | --- | --- |
| 4A | 6-(4-Fluoro-benzenesulfonyl)-2H-pyridazin-3-one | >225 |
| 4B | 6-(4-Trifluoromethyl-benzenesulfonyl)-2H-pyridazin-3-one | >220 |
| 4C | 6-(2-Bromo-benzenesulfonyl)-2H-pyridazin-3-one | 210–213 |
| 4D | 6-(3,4-Dichloro-benzenesulfonyl)-2H-pyridazin-3-one | 166–168 |
| 4E | 6-(4-Methoxy-benzenesulfonyl)-2H-pyridazin-3-one | 111–113 |
| 4F | 6-(2-Chloro-4-fluoro-benzenesulfonyl)-2H-pyridazin-3-one | 205–208 |
| 4G | 6-(4-Chloro-benzenesulfonyl)-2H-pyridazin-3-one | >220 |
| 4H | 6-(2-Chloro-benzenesulfonyl)-2H-pyridazin-3-one | 220–222 |
| 4I | 6-(3-Bromo-benzenesulfonyl)-2H-pyridazin-3-one | >220 |
| 4K | 6-(4-Bromo-2-fluoro-phenylmethanesulfonyl)-2H-pyridazin-3-one | >220 |
| 4L | 6-(2,6-Dichloro-phenylmethanesulfonyl)-2H-pyridazin-3-one | 219–220 |
| 4M | 6-(3-Chloro-5-methyl-benzenesulfonyl)-2H-pyridazin-3-one | >250 |
| 4N | 6-(2-Chloro-4,6-difluoro-benzenesulfonyl)-2H-pyridazin-3-one | >250 |

EXAMPLE 5

6-(2,4-Dichloro-benzenesulfonyl)-2H-pyridazin-3-one
Step A: 6-(2,4-Dichloro-phenylsulfanyl)-2H-pyridazin-3-one. Potassium t-butoxide (1.1 g) was added to a solution of 2,4-dichlorothiophenol (1.8 g) in N,N-dimethylformamide (DMF) (5 mL). The mixture was stirred at room temperature for 10 minutes and then 6-chloro-2H-pyridazin-3-one (1.31 g) was added. The reaction mixture was stirred at 100° C. for five hours. The mixture was then cooled to room temperature, poured into water (20 mL) and 20% potassium hydroxide (5 mL) was added. The resulting dark solution was extracted with ethyl acetate (2×10 mL). The aqueous layer was collected and the pH was adjusted to 3 with concentrated hydrochloric acid. The solution was then extracted with ethyl acetate (3×10 mL). The ethyl acetate layer was collected, dried over anhydrous sodium sulfate, filtered and evaporated to obtain a crude product, which was purified by silica gel chromatography (1:1 ethyl acetate/hexane as eluent) to afford 6-(2,4-dichloro-phenylsulfanyl)-2H-pyridazin-3-one (418 mg, 15%); NMR 6.88 (d, 1H), 7.10 (d, 1H), 7.24(dd, 1H), 7.48 (d, 1H), 7.52 (d, 1H).

Step B: 6-(2,4-Dichloro-benzenesulfonyl)-2H-pyridazin-3-one. A mixture of 6-(2,4-dichloro-phenylsulfanyl)-2H-pyridazin-3-one (418 mg), peracetic acid (3.2 mL) and acetic acid (3.2 mL) was prepared and stirred for 2.5 hours at 80° C. The reaction mixture was then cooled to room temperature and poured into water (50 mL). The resulting white solid was collected and dried to obtain the title product, 6-(2,4-dichloro-benzenesulfonyl)-2H-pyridazin-3-one, (37%, 173 mg); mp, 202–203° C.; NMR 7.15 (d, 1H), 7.81 (dd, 1H), 8.03 (m, 2H), 8.25 (d, 1H), 13.88 (s, 1H).

Examples 5A to 5I were prepared from the appropriate starting materials in a manner analogous to the method of Example 5.

| Example | Compound | MP ° C. |
|---|---|---|
| 5A | 6-(2-Chloro-benzenesulfonyl)-2H-pyridazin-3-one | 220–222 |
| 5B | 6-(2,4-Difluoro-benzenesulfonyl)-2H-pyridazin-3-one | 186–188 |
| 5C | 6-(Naphthalene-1-sulfonyl)-2H-pyridazin-3-one | 225–226 |
| 5D | 6-(2,4-Dichloro-benzenesulfonyl)-2H-pyridazin-3-one | 202–203 |
| 5E | 6-(2-Fluoro-benzenesulfonyl)-2H-pyridazin-3-one | 189–191 |
| 5F | 6-(2,3-Dichloro-benzenesulfonyl)-2H-pyridazin-3-one | 224–225 |
| 5G | 6-(2,5-Dichloro-benzenesulfonyl)-2H-pyridazin-3-one | 229–232 |
| 5H | 6-(2,6-Dichloro-benzenesulfonyl)-2H-pyridazin-3-one | 118–120 |
| 5I | 6-(2,3-Difluoro-benzenesulfonyl)-2H-pyridazin-3-one | >225 |

EXAMPLE 6

6-(2-Hydroxy-benzenesulfonyl)-2H-pyridazin-3-one

A mixture of 6-(2-methoxy-benzenesulfonyl)-2H-pyridazin-3-one (100 mg) and aluminum tri-bromide (2 g) was prepared and heated at 100° C. for two hours. The reaction mixture was cooled and water (10 mL) was added. The mixture was then extracted with chloroform. The organic extract was washed with water (2×10 mL), dried over anhydrous sodium sulfate and evaporated. The resulting residue was triturated with isopropyl ether and the resulting solid was collected by filtration to afford the title compound (61%, 58 mg), $^1$HNMR (CDCl$_3$, 300 MHz), δ 7.0 (m, 3H), 7.6 (m, 2H), 7.8 (d, 1H).

EXAMPLE 7

3-(2-Chloro-benzenesulfonyl)-6-methoxy-pyridazine, N-oxide

A mixture of 3-(2-chloro-phenylsulfanyl)-6-methoxy-pyridazine, m-chloroperbenzoic acid (MCPBA) (4.0 g), and chloroform (30 mL) was prepared and refluxed for 30 hours. Mass spectrum analysis of an aliquot of the reaction sample showed complete conversion to the desired sulfone-N-oxide (M+, 301). The reaction was cooled, washed successively with sodium sulfite (10% solution, 20 mL), sodium carbonate (10% solution, 20 mL), and water (2×20 mL). The chloroform layer was collected, dried over anhydrous sodium sulfate, filtered and the filtrate was evaporated to obtain a crude solid. The crude solid was purified by silica gel chromatography (1:1 ethyl acetate/hexane as eluent) to afford the title compound (38%, 425 mg); mp, 148–153° C.; (38%, 425 mg); NMR δ 4.01 (s, 3H), 6.80 (d, 1H), 7.42 (m, 1H), 7.57 (m, 2H), 8.38 (d, 1H), 8.46 (m, 1H).

EXAMPLE 8

3-(2-Chloro-4-fluoro-benzenesulfonyl)-6-methoxy-pyridazine, N-oxide

The title compound was prepared according to a procedure analgous to that of Example 7 using 3-(2-chloro-4-fluoro-phenylsulfanyl)-6-methoxy-pyridazine as the starting compound. (60%); mp, 159–161° C.; NMR δ 4.01 (s, 3H), 6.80 (d, 1H), 7.15 (dd, 1H), 7.25 (dd, 1H), 8.37 (d, 1H), 8.49 (m, 1H).

EXAMPLE 9

3-(2-Chloro-benzenesulfonyl)-6-methoxy-pyridazine

A mixture of 3-(2-chloro-benzenesulfonyl)-6-methoxy-pyridazine, N-oxide, N-oxide from Example 7 (317 mg) and triethyphosphite (3 mL) was heated to 100° C. for four hours. The reaction mixture was cooled to room temperature, poured into water (20 mL), and extracted with ethyl acetate (2×10 mL). The organic extract was evaporated to dryness and the crude product was purified by silica gel chromatography (1:1 ethyl acetate/hexane as eluent). (48%, 143 mg); NMR δ 4.19 (s, 3H), 7.19 (d, 1H), 7.43 (dd, 2H), 7.58 (m, 2H), 8.27 (d, 1H), 8.44 (dd, 2H).

EXAMPLE 10

3-(2-Chloro-4-fluoro-benzenesulfonyl)-6-methoxy-pyridazine

The title compound was prepared according to procedure of Example 9 starting from 3-(2-chloro-4-fluoro-benzenesulfonyl)-6-methoxy-pyridazine, N-oxide. (48%); mp, 84–87° C.

EXAMPLE 11

6-Methoxy-pyridazine-3-sulfonyl fluoride

Step A: 6-Methoxy-pyridazine-3-thiol. A mixture of 3-chloro-6-methoxy-pyridazine (100 g), thiourea (105 g) and ethyl methyl ketone (1.8 L) was prepared and refluxed for three hours. The reaction mixture was then cooled and the supernatant was poured into water and extracted with 1M sodium hydroxide (4×100 mL). The sodium hydroxide solution was washed with ethyl acetate (2×50 mL) and the aqueous extract was acidified with sufficient concentrated hydrochloric acid to lower the pH to 5. The resulting yellow solid was collected and air dried to afford the title compound (24%, 23 g); mp, 198–200° C.

Step B: 6-Methoxy-pyridazine-3-sulfonyl fluoride. A mixture of 6-methoxy-pyridazine-3-thiol (7.1 g), methanol (100 mL), water (100 mL), and potassium hydrogen fluoride (39 g) was prepared and stirred at −10° C. for 30 minutes. Chlorine gas was bubbled into the mixture at a rate to ensure that the temperature did not exceed −10° C. The whitish-yellow reaction mixture was then poured into ice-cold water (50 mL) and the resulting white solid was filtered and air dried to afford the title compound (74%, 7.1 g); mp, 87–88° C.

EXAMPLE 12

6-Oxo-1,6-dihydro-pyridazine-3-sulfonic acid methyl-phenyl-amide

Step A: 6-Methoxy-pyridazine-3-sulfonic acid methyl-phenyl-amide. A mixture was prepared of 6-methoxy-pyridazine-3-sulfonyl fluoride from Example 11 (1.62 mmol, 312 mg) and N-methyl aniline (24.3 mmol, 0.26 mL) and heated at 100° C. for 12 hours. The mixture was then cooled. The resulting solid residue was purified by silica gel chromatography to isolate the title compound (53%, 240 mg); $M^+$, 279.

Step B: 6-Oxo-1,6-dihydro-pyridazine-3-sulfonic acid methyl-phenyl-amide. A mixture of 6-methoxy-pyridazine-3-sulfonic acid methyl-phenyl-amide (239 mg), dioxane (4 mL) and concentrated hydrochloric acid (1 mL) was prepared and refluxed for one hour. The mixture was then evaporated to dryness. The resulting solid was triturated with water and the solid was collected to afford the title compound (75%, 171 mg); mp, 157–158° C.

EXAMPLE 13

6-Oxo-1,6-dihydro-pyridazine-3-sulfonic acid isopropyl-phenyl-amide

The title compound was prepared according to a procedure analogous to that of Example 12 for 6-oxo-1,6-dihydro-pyridazine-3-sulfonic acid methyl-phenyl-amide, substituting N-isopropylaniline for N-methyl aniline in step 3, (20%); mp, 190–191° C.

EXAMPLE 14

6-Oxo-1,6-dihydro-pyridazine-3-sulfonic acid (3,4-dichloro-phenyl)-methyl-amide The title compound was prepared according to a procedure analogous to that of Example 12 for 6-oxo-1,6-dihydro-pyridazine-3-sulfonic acid methyl-phenyl-amide, substituting N-methyl-3,4-dichloroaniline for N-methylaniline (28%); mp, 207–208° C.

EXAMPLE 15

6-(4-Fluoro-phenylsulfanyl)-2H-pyridazin-3-one

A mixture of 3-(4-fluoro-phenylsulfanyl)-6-methoxy-pyridazine (250 mg), prepared by a procedure analogous to step A of Example 2, and concentrated hydrochloric acid was prepared and refluxed for 30 minutes. The mixture was then evaporated to dryness. The resulting residue was purified by silica gel chromatography (ethyl acetate as eluent) to afford the title compound (65%, 152 mg); mp, 99–101° C.

EXAMPLE 16

6-(Biphenyl-4-sulfonyl)-2H-pyridazin-3-one

Step A: 3-(Biphenyl-4-sulfonyl)-6-methoxy-pyridazine. A mixture of 4-fluoro-benzene boronic acid (157 mg) 3-(4-fluoro-benzensulfonyl)-6-methoxy-pyridizine (247 mg), potassium carbonate (207 mg), $Pd[P(Ph)_3]_4$ (87 mg), toluene (4 mL), ethanol (2 mL) and water (1.5 mL) was prepared and refluxed for four hours. The mixture was cooled and water was added (10 mL). The mixture was then filtered and the resulting filtrate was extracted with ethyl acetate (20 mL). The ethyl acetate extract was washed with water and the ethyl acetate portion was collected and dried with anhydrous sodium sulfate and filtered. The filtrate was collected and evaporated to dryness to afford the title product of step A. NMR δ 4.17 (s, 3H), 7.13 (m, 3H), 7.54 (m, 2H), 7.70 (m, 2H), 8.17 (m,3H).

Step B: 6-(Biphenyl-4-sulfonyl)-2H-pyridazin-3-one. The product of step A was treated with concentrated hydrochloric acid according to step C of Example 2 to obtain the title compound. Mp. 219–220° C.

EXAMPLE 17

6-Benzyloxy-pyridazine-3-sulfonyl fluoride

Step A: 3-Benzyloxy-6-chloro-pyridazine. Sodium metal (3.1 g) was added to benzyl alcohol (75 mL) and gently warmed to 50° C. for 30 minutes until all the sodium metal dissolved. A solution of 3,6-dichloropyridazine (135 mmol) in benzyl alcohol (75 mL) was added. The reaction mixture was kept at 100° C. for 24 hours. Excess benzyl alcohol was evaporated and the residue was extracted with ethyl acetate (3×100 mL) and the ethyl acetate extract was washed with water. The resulting ethyl acetate layer was collected, dried, filtered, and the filtrate was evaporated to afford the title compound (90%, 26.7 g); mp, 77–78° C.

Step 2: 6-Benzyloxy-pyridazine-3-thiol. A mixture of 3-benzyloxy-6-chloro-pyridazine (4 g), thiourea (2.8 g) and ethyl methyl ketone (75 mL) was prepared and refluxed overnight. Excess ethyl methyl ketone was evaporated and the resulting residue was extracted with 2M sodium hydroxide (25 mL). The sodium hydroxide solution was then washed with ethyl acetate (2×30 mL). The aqueous layer was collected and sufficient concentrated hydrochloric acid was added to bring the pH to 5. The resulting solution was extracted with ethyl acetate (2×30 mL). The ethyl acetate extract was collected, dried, filtered, and the filtrate was evaporated to afford the title compound (15%, 605 mg); mp, 155–157° C.

Step 3: 6-Benzyloxy-pyridazine-3-sulfonyl fluoride. A mixture of 6-benzyloxy-pyridazine-3-thiol (510 mg), methanol (10 mL), water (10 mL), and potassium hydrogen fluoride (1.83 g) was prepared and stirred at −10° C. for 30 minutes. Chlorine gas was bubbled into the mixture at a rate to ensure that the temperature not exceed −10° C. The resulting whitish-yellow reaction mixture was poured into ice cold water (50 mL) and the resulting white solid was filtered and air-dried to afford the title compound. (Yield 89%, 560 mg); mp, 85–86° C.

EXAMPLE 18

6-[2-(4-Chloro-phenyl)-2-oxo-ethanesulfonyl]-2H-pyridazin-3-one

Step A: 1-(4-Chloro-phenyl)-2-(6-methoxy-pyridazin-3-ylsulfanyl)-ethanone. A mixture of 2-mercapto-6-methoxy-pyridazine (1.42 g), 4-chloro-α-bromo acetophenone (10 mmol, 2.33 g), potassium carbonate (2.76 g), and dimethyl formamide (15 mL) was stirred at room temperature for one hour. The reaction mixture was filtered, the residue was washed with ethyl acetate (2×20 mL) and the combined filtrate was washed with water (2×20 mL). The ethyl acetate layer was collected, dried, filtered and the filtrate was evaporated to dryness to afford the title compound of step A (96%, 2.85 g); mass spectrum, $m^+295$.

Step B: 1-(4-Chloro-phenyl)-2-(6-methoxy-pyridazine-3-sulfonyl)-ethanone. A mixture of the compound from step A, (8.5 mmol, 2.3 g), MCPBA (25 mmol, 5.8 g), and methylene chloride (160 mL) was stirred at room temperature for 40 min. To the reaction mixture was added a saturated solution of sodium bi-carbonate (400 mL) and the methylene chloride layer was collected, dried, filtered and the filtrate was evaporated to afford the title compound of step B as a white solid (79%, 2.2 g); mp, 153–156° C.

Step C: 6-[2-(4-Chloro-phenyl)-2-oxo-ethanesulfonyl]-2H-pyridazin-3-one.

The compound from step B was transformed to the title compound, through acid hydrolysis, according to Step C, of Example 2; (79%); mp, >240° C.

EXAMPLE 19

6-[2-(4-Chloro-phenyl)-2-hydroxy-ethanesulfonyl]-2H-pyridazin-3-one

A suspension was prepared of 6-[2-(4-chloro-phenyl)-2-oxo-ethanesulfonyl]-2H-pyridazin-3-one (1.0 mmol, 312 mg) prepared according to Example 18 in methanol (10 mL). Sodium borohydride (1.5 mmol, 55 mg) was added to the suspension at room temperature and stirred for 1 hour. The reaction mixture was evaporated and the residue was triturated with 10% hydrochloric acid (5 mL). The resulting white precipitate was filtered and air-dried to afford the title compound (69%, 218 mg); mp, 178–179° C.

EXAMPLE 20

Protocol for Determination of Aldose Reductase Inhibition

Test compound (TC) solutions were prepared by dissolving TC in 20 μl 20% dimethylsulfoxide (DMSO) and diluting with 100 mM potassium phosphate buffer, pH 7.0, to various TC concentrations, typically ranging from 5 mM to 1 μM. A "zero TC" solution was prepared that started with only 20 μl DMSO (no TC). The assay for aldose reductase activity was performed in a 96-well plate. Initiation of the reaction (with substrate) was preceded by a 10 minute pre-incubation at 24° C. of 200 μl 100 mM potassium phosphate buffer, pH 7.0, containing 125 μM NADPH and 12.5 nM human recombinant Aldose Reductase (Wako Chemicals, Inc., #547–00581) with 25 μl TC solution. The reaction was initiated by the addition of 25 μl 20 mM D-glyceraldehyde (Sigma, St. Louis). The rate of decrease in $OD_{340}$ was monitored for 15 minutes at 24° C. in a 340 ATTC Plate Reader (SLT Lab Instruments, Austria). Inhibition by TC was measured as the percentage decrease in the rate of NADPH oxidation as compared to a non-TC containing sample.

What is claimed is:

1. A therapeutic method comprising administering to a mammal in need of treatment or prevention of tissue damage resulting from ischemia an effective amount of a compound of formula I

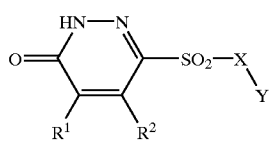

I or a prodrug of said compound, or a pharmaceutically acceptable salt of said compound or said prodrug, wherein:

$R^1$ and $R^2$ are each independently hydrogen or methyl;

X and Y together are $CH_2$—CH(OH)—Ar or $CH_2$—C(O)—Ar, or

X is a covalent bond, $NR^3$ or $CHR^4$, wherein, $R^3$ is $(C_1-C_3)$alkyl or a phenyl that is optionally substituted with one or more substituents selected from OH, F, Cl, Br, I, CN, $CF_3$, $(C_1-C_6)$alkyl, O—$(C_1-C_6)$alkyl, $S(O)_n$—$(C_1-C_8)$alkyl and $SO_2$—$NR^5R^6$, and $R^4$ is hydrogen or methyl, and Y is a phenyl or naphthyl ring optionally substituted with one or more substituents selected from Ar, OH, F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^5R^6$;

Ar is a phenyl or naphthyl ring optionally substituted with one or more substituents selected from F, Cl, Br, I, CN, $CF_3$, $(C_1-C_6)$alkyl, O—$(C_1-C_6)$alkyl, $S(O)_n$—$(C_1-C_6)$alkyl and $SO_2$—$NR^5R^6$;

n is independently for each occurrence 0, 1 or 2;

$R^5$ is independently for each occurrence H, $(C_1-C_6)$alkyl, phenyl or naphthyl; and $R^6$ is independently for each occurrence $(C_1-C_6)$alkyl, phenyl or naphthyl.

2. A therapeutic method of claim 1 wherein said compound is selected from:

6-(2-chloro-benzenesulfonyl)-2H-pyridazin-3-one;
6-(3-chloro-benzenesulfonyl)-2H-pyridazin-3-one;
6-(2,3-dichloro-benzenesulfonyl)-2H-pyridazin-3-one
6-(2,5-dichloro-benzenesulfonyl )-2H-pyridazin-3-one;
6-(4-fluoro-benzenesulfonyl)-2H-pyridazin-3-one;
6-(4-chloro-benzenesulfonyl)-2H-pyridazin-3-one;
6-(2-fluoro-benzenesulfonyl)-2H-pyridazin-3-one;
6-(2,3-difluoro-benzenesulfonyl)-2H-pyridazin-3-one;
6-(2,4-dichloro-benzenesulfonyl)-2H-pyridazin-3-one;
6-(2,4-difluoro-benzenesulfonyl)-2H-pyridazin-3-one;
6-(2,6-dichloro-benzenesulfonyl)-2H-pyridazin-3-one;
6-(2-chloro-4-fluoro-benzenesulfonyl)-2H-pyridazin-3one;
6-(2-bromo-4-fluoro-benzenesulfonyl)-2H-pyridazin-3one; and
6-(naphthalene-1-sulfonyl)-2H-pyridazin-3-one; or a prodrug of a compound selected therefrom, or a pharmaceutically acceptable salt of said compound or said prodrug.

3. A therapeutic method of claim 2 wherein said compound is selected from:

6-(2-chloro-benzenesulfonyl)-2H-pyridazin-2-one;
6-(3-chloro-benzenesulfonyl)-2H-pyridazin-3-one;
6-(2,3-dichloro-benzenesulfonyl)-2H-pyridazin-3one;
6-(2,5-dichloro-benzenesulfonyl)-2H-pyridazine-3one;
6-(2,3-difluoro-benzenesulfonyl)-2H-pyridazin-3one;
6-(2,4-dichloro-benzenesulfonyl)-2H-pyridazin-3one;
6-(2,4-difluoro-benzensulfonyl)-2H-pyridazin-3one;
6-(2,6-dichloro-benzenesulfonyl)-2H-pyridazin-3-one;
6-(2-chloro-4-fluoro-benzenesulfonyl)-2H-pyridazin-3one;
6-(2-bromo-4-fluoro-benzenesulfonyl)-2H-pyridazin-3one; and
6-(naphthalene-1-sulfonyl)-2H-pyridazin-3-one, or a prodrug of a compound selected therefrom, or a pharmaceutically acceptable salt of said compound or said prodrug.

4. A therapeutic method of claim 3 wherein said compound is a selected from:

6-(2,3-difluoro-benzenesulfonyl)-2H-pyridazin-3-one;
6-(2,4-dichloro-benzenesulfonyl)-2H-pyridazin-3-one;
6-(2-bromo-4-fluoro-benzenesulfonyl)-2H-pyridazin-3-one; and 6-(naphthalene-1-sulfonyl)-2H-pyridazin-3-one, or a prodrug of a compound selected therefrom, or a pharmaceutically acceptable salt of said compound or said prodrug.

5. A therapeutic method of claim 1 wherein said tissue is heart, brain, liver, kidney, lung, gut, skeletal muscle, spleen, pancreas, retina or intestinal tissue.

6. A therapeutic method of claim 2 wherein said tissue is heart, brain, liver, kidney, lung, gut, skeletal muscle, spleen, pancreas, retina or intestinal tissue.

7. A therapeutic method of claim 3 wherein said tissue is heart, brain, liver, kidney, lung, gut, skeletal muscle, spleen, pancreas, retina or intestinal tissue.

8. A therapeutic method of claim 4 wherein said tissue is heart, brain, liver, kidney, lung, gut, skeletal muscle, spleen, pancreas, retina or intestinal tissue.

9. A therapeutic method of claim 1 wherein said tissue is heart tissue.

10. A therapeutic method of claim 2 wherein said tissue is heart tissue.

11. A therapeutic method of claim 3 wherein said tissue is heart tissue.

12. A therapeutic method of claim 4 wherein said tissue is heart tissue.

13. A therapeutic method of claim 1 wherein said compound of formula I, said prodrug, or said pharmaceutically acceptable salt of said compound or said prodrug is administered in an aldose reductase inhibiting amount.

14. A therapeutic method of claim 2 wherein said compound of formula I, said prodrug, or said pharmaceutically acceptable salt of said compound or said prodrug is administered in an aldose reductase inhibiting amount.

15. A therapeutic method of claim 3 wherein said compound of formula I, said prodrug, or said pharmaceutically acceptable salt of said compound or said prodrug is administered in an aldose reductase inhibiting amount.

16. A therapeutic method of claim 4 wherein said compound of formula I, said prodrug, or said pharmaceutically acceptable salt of said compound or said prodrug is administered in an aldose reductase inhibiting amount.

17. A therapeutic method of claim 1 wherein said mammal is a human.

18. A therapeutic method of claim 2 wherein said mammal is a human.

19. A therapeutic method of claim 3 wherein said mammal is a human.

20. A therapeutic method of claim 4 wherein said mammal is a human.

21. A therapeutic method of claim 1 wherein said tissue is heart tissue, said compound of formula I, said prodrug, or said pharmaceutically acceptable salt of said compound or said prodrug is administered in a aldose reductase inhibiting amount and said mammal is a human.

22. A therapeutic method of claim 2 wherein said tissue is heart tissue, said compound of formula I, said prodrug, or said pharmaceutically acceptable salt of said compound or said prodrug is administered in a aldose reductase inhibiting amount and said mammal is a human.

23. A therapeutic method of claim 3 wherein said tissue is heart tissue, said compound of formula I, said prodrug, or said pharmaceutically acceptable salt of said compound or said prodrug is administered in a aldose reductase inhibiting amount and said mammal is a human.

24. A therapeutic method of claim 4 wherein said tissue is heart tissue, said compound of formula I, said prodrug, or said pharmaceutically acceptable salt of said compound or said prodrug is administered in a aldose reductase inhibiting amount and said mammal is a human.

* * * * *